United States Patent
Wang et al.

(10) Patent No.: US 9,861,331 B2
(45) Date of Patent: Jan. 9, 2018

(54) METHOD FOR SCANOGRAM SCANS IN PHOTON-COUNTING COMPUTED TOMOGRAPHY

(71) Applicant: TOSHIBA MEDICAL SYSTEMS CORPORATION, Otawara-Shi (JP)

(72) Inventors: Xiaolan Wang, Buffalo Grove, IL (US); Yuexing Zhang, Naperville, IL (US); Satoru Nakanishi, Arlington Heights, IL (US)

(73) Assignee: Toshiba Medical Systems Corporation, Otawara-shi (JP)

(*) Notice: Subject to any disclaimer, the term of this patent is extended or adjusted under 35 U.S.C. 154(b) by 214 days.

(21) Appl. No.: 14/594,876

(22) Filed: Jan. 12, 2015

(65) Prior Publication Data

US 2016/0199016 A1    Jul. 14, 2016

(51) Int. Cl.
| | | |
|---|---|---|
| G01N 23/00 | (2006.01) | |
| A61B 6/00 | (2006.01) | |
| A61B 6/03 | (2006.01) | |
| G01T 1/29 | (2006.01) | |

(52) U.S. Cl.
CPC .............. *A61B 6/488* (2013.01); *A61B 6/032* (2013.01); *A61B 6/4241* (2013.01); *A61B 6/4266* (2013.01); *G01T 1/2985* (2013.01)

(58) Field of Classification Search
None
See application file for complete search history.

(56) References Cited

U.S. PATENT DOCUMENTS

| | | | | |
|---|---|---|---|---|
| 7,142,636 | B2* | 11/2006 | Hsieh | A61B 6/032 348/E5.086 |
| 2006/0256920 | A1* | 11/2006 | Tsujii | A61B 6/02 378/114 |
| 2013/0251097 | A1* | 9/2013 | Zou | A61B 6/032 378/9 |
| 2015/0146844 | A1* | 5/2015 | Zamyatin | A61B 6/032 378/5 |

\* cited by examiner

*Primary Examiner* — Andrew Smyth
(74) *Attorney, Agent, or Firm* — Oblon, McClelland, Maier & Neustadt, L.L.P.

(57) ABSTRACT

A computed tomography (CT) imaging apparatus for performing a scanogram includes a radiation source to emit X-rays; a plurality of photon-counting detectors (PCDs) arranged in a circular ring between the radiation source and a CT detector; and processing circuitry to perform a first scan to obtain projection data; determine a plurality of dark channels by comparing the obtained projection data to a predetermined threshold; add at least one adjacent padding channel to the determined plurality of dark channels to determine a plurality of shadowed channels; generate a correction map from the determined plurality of shadowed channels; and correct a scanogram obtained by a second scan based on the generated correction map. The apparatus reduces the shadow effects in the scanogram scan.

12 Claims, 8 Drawing Sheets

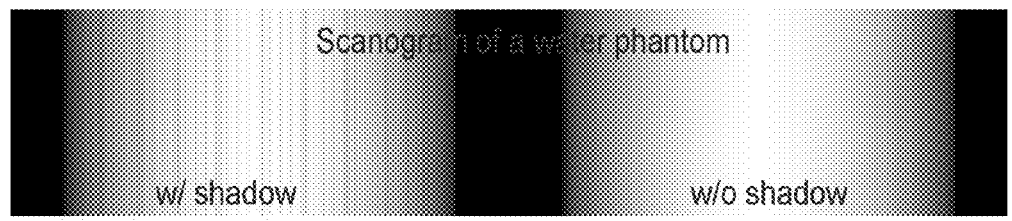
*Fig. 3C*
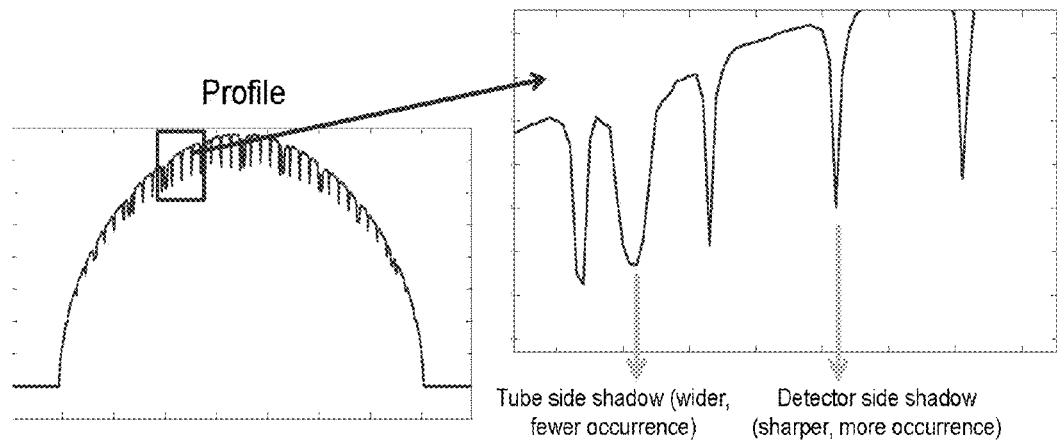
*Fig. 3D*  *Fig. 3E*

METHOD FOR SCANOGRAM SCANS IN PHOTON-COUNTING COMPUTED TOMOGRAPHY

FIELD

The exemplary embodiments described herein relate to computed tomography (CT) systems with photon-counting detectors (PCDs).

BACKGROUND

Traditional CT scanners use energy-integrating detectors for acquiring energy integration X-ray data. An energy-integrating detector does not take advantage of the energy information in the X-ray beam. Even though the X-ray source emits X-rays in a broad spectrum, the detector is not able to differentiate between photons of different energy, but delivers an output signal proportional to the total energy of the photons registered during the readout interval. To obtain the spectral nature of the transmitted X-ray data, a photon-counting detector splits the X-ray beam into its component energies or spectrum bins and counts a number of photons in each of the bins. The use of the spectral nature of the X-ray source in CT is often referred to as spectral CT. Spectral CT imaging provides material separation capabilities that can potentially enable new clinical applications. The spectral images are usually presented as material concentration images of basis materials or mono-energetic images. For example, spectral CT is used in discriminating tissues, differentiating between materials such as tissues containing calcium and iodine, or enhancing the detection of smaller vessels. Among other advantages, spectral CT is also expected to reduce beam-hardening artifacts and to increase accuracy in CT numbers independent of scanners.

Currently, most conventional designs acquire spectral information using either high- and low-energy X-ray sources or dual-detector-layer technologies. To improve the accuracy of material separation, photon-counting detector technologies can be used to provide good energy resolution. Photon-counting energy-resolved direct-conversion semiconductor detectors for computed tomography (CT) allow exploitation of the spectral information of each incident photon. X-ray photons interacting with the semiconductor sensors can be converted directly to electron-hole pairs without any inefficient intermediate processes, ensuring the superior intrinsic energy resolution.

Before a clinical CT scan, a scanogram is performed to locate anatomical landmarks and anatomical regions for scan prescription. Both the X-ray tube and the detector remain stationary, while the patient bed travels at a constant speed. A scanogram image is similar to a radiograph, and is non-diagnostic. The scanogram generally requires air scan data and the scanogram image is obtained after subtracting the air scan data in a log scale.

However, for photon-counting CT, sparsely distributed stationary photon-counting detectors (PCDs) are distributed in front of a third-generation integrated detector, and create shadows on the third-generation integrated detector during scanogram scans. These shadows cause missing data and severely degrade the quality of the scanogram images.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein:

FIG. 3C illustrates an exemplary scanogram of a water phantom;

FIG. 3D illustrates an exemplary scanogram profile of the water phantom;

FIG. 3E illustrates an expanded view of the exemplary scanogram profile of the water phantom in FIG. 3D;

DETAILED DESCRIPTION

In one embodiment, there is provided a computed tomography (CT) imaging apparatus, comprising: (1) a radiation source configured to emit X-rays; (2) a plurality of photon-counting detectors (PCDs) arranged in a circular ring between the radiation source and a CT detector; and (3) processing circuitry configured to perform a first scan to obtain first projection data; determine a plurality of dark channels by comparing the obtained projection data to a predetermined threshold; add at least one adjacent padding channel to the determined plurality of dark channels to determine a plurality of shadowed channels; generate a correction map from the determined plurality of shadowed channels; and correct a scanogram based on the generated correction map.

In another embodiment, there is provided, a computed tomography (CT) imaging method for a CT apparatus that includes a plurality of photon-counting detectors (PCDs) arranged in a circular ring between a radiation source and a CT detector, the method comprising: (1) performing a first scan to obtain first projection data; (2) determining a plurality of dark channels by comparing the obtained projection data to a predetermined threshold; (3) adding at least one adjacent padding channel to the determined plurality of dark channels to determine a plurality of shadowed channels; (4) generating a correction map from the determined plurality of shadowed channels; and (5) correcting a scanogram obtained by a second scan based on the generated correction map.

In another embodiment, there is provided, a computed tomography (CT) imaging method for a CT apparatus that includes a plurality of photon-counting detectors (PCDs) arranged in a circular ring between a radiation source and a CT detector, the method comprising: (1) positioning the X-ray tube at a first position; (2) performing a first scan to obtain first projection data; (3) determining a plurality of dark channels by comparing the obtained first projection data to a predetermined threshold; (4) generating a correction map from the determined plurality of dark channels; (5) conducting a first scanogram scan of the patient with the X-ray tube at the first position, without moving the X-ray tube, to obtain first scanogram data; and (6) correcting the obtained first scanogram data using the generated correction map.

Figure 1:
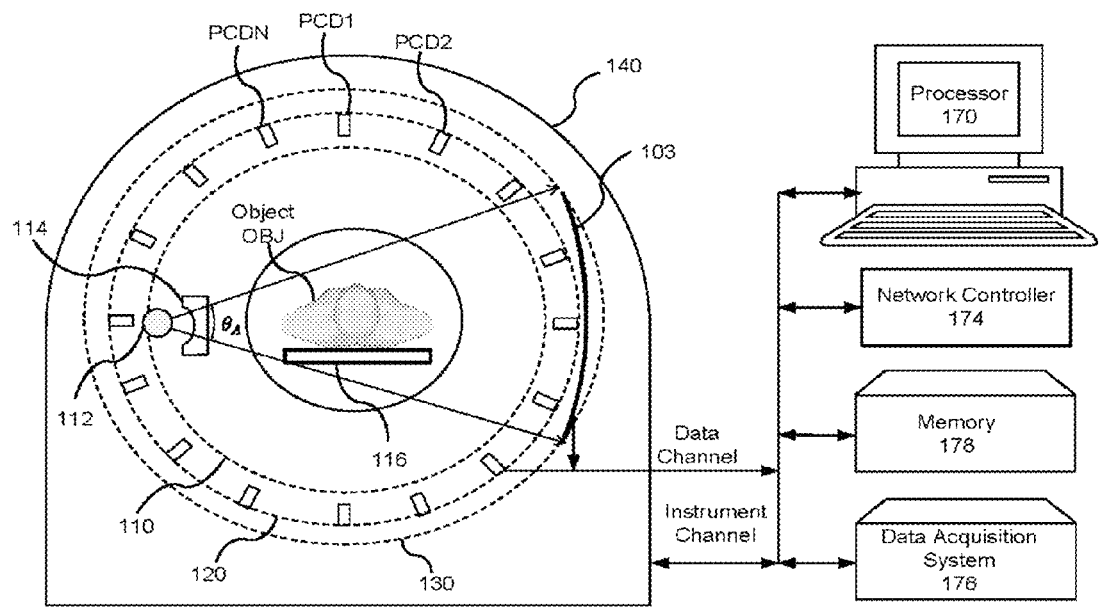
FIG. 1 shows a schematic diagram of an implementation of an image reconstruction apparatus having a coupled-ring topology.
Figure 2:
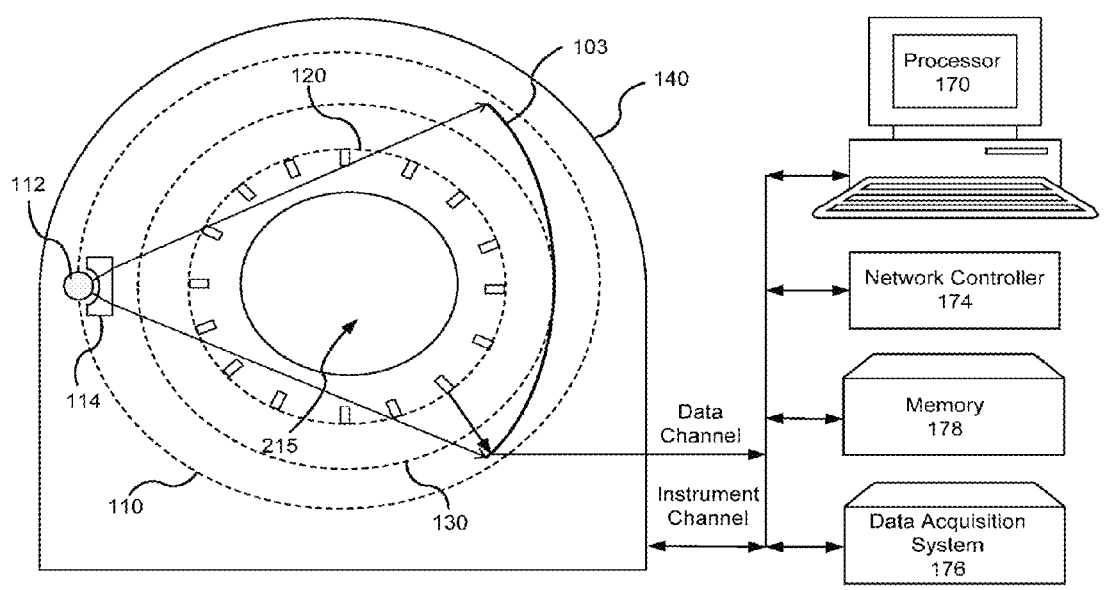
FIG. 2 shows a schematic diagram of an implementation of an image reconstruction apparatus having an inner-ring topology.

FIG. 1 and FIG. 2 show schematic views of CT scanner systems with hybrid systems having energy-integrating detectors arranged in a third-generation geometry and photon-counting detectors (PCDs) arranged in a fourth-generation geometry. FIG. 1 shows a coupled-ring topology with the X-ray source 112 inside the ring of PCDs and the X-ray detector unit 103 outside the ring of PCDs, as discussed in U.S. patent application Ser. No. 13/426,903, incorporated herein by reference in its entirety. In contrast, FIG. 2 shows an inner-ring topology with both the X-ray source 112 and the X-ray detector unit 103 outside the ring of PCDs, as discussed in U.S. patent application Ser. No. 14/092,998, incorporated herein by reference in its entirety.

Illustrated in FIG. 1 is an implementation for placing the PCDs in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector unit 103.

Also shown in FIG. 1 is circuitry and hardware for acquiring, storing, processing, and distributing X-ray projection data. The circuitry and hardware include: a processor 170, a network controller 174, a memory 178, and a data acquisition system 176.

In one implementation, the X-ray source 112 and the collimator/filter 114 are fixedly connected to a rotational component 110 that is rotatbly connected to a gantry 140. The X-ray detector is similarly fixedly connected to a rotational component 130 that is rotatably connected to the gantry 140. While, the PCDs are fixedly connected to a circular component 120 that is fixedly connected to the gantry 140. The gantry 140 houses many pieces of the CT scanner.

The gantry of the CT scanner also includes an open aperture 215 (shown in FIG. 2) enabling the object OBJ that is arranged on a table 116 positioned in a projection plane of the X-rays traveling from the X-ray source to the PCDs and detector unit 203. The "projection plane" is a volume wherein X-rays pass from the X-ray source 112 to the detectors including the PCDs and the detector unit 103. The "object space" is the intersection of the projection plane and the open aperture 215 of the gantry. The "image space" includes the union of projection planes corresponding to all projection angles of the X-ray source 112 as the X-ray source 112 rotates around the aperture of the gantry. The image space is generally larger than the object space enabling image reconstruction for a volume extending beyond the aperture of the gantry and into the structure of the gantry 140.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 1 includes a detector unit 103 having energy-integrating detectors arranged in a conventional third-generation geometry. The detector elements in the detector unit 103 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 120 in a gantry. In one implementation, the photon-counting detectors PCD1 through PCDN are fixedly placed on the circular component 120 at predetermined equidistant positions. In an alternative implementation, the photon-counting detectors PCD1 through PCDN are fixedly placed on the circular component 120 at predetermined non-equidistant positions. The circular component 120 remains stationary with respect to the object OBJ and does not rotate during the data acquisition.

Both the X-ray source 112, collimator 114 (e.g., a bow-tie filter), and the detector unit 103 rotate around the object OBJ while the photon-counting detectors PCD1 through PCDN are stationary with respect to the object OBJ. In one implementation, the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 is mounted at a diametrically opposed position from the X-ray source 112 across the object OBJ and rotates outside the stationary circular component 120, on which the photon-counting detectors PCD1 through PCDN are fixed in a predetermined sparse arrangement.

In one implementation, the X-ray source 112 optionally travels a helical path relative to the object OBJ, wherein the table 116 moves the object OBJ linearly in a predetermined direction perpendicular to the rotational plane of the rotational portion 110 as the rotational portion 110 rotates the X-ray source 112 and detector unit 103 in the rotational plane.

The motion of the rotational portion 110 around the object OBJ is controlled by a motion control system. The motion control system can be integrated with a data acquisition system or can be separate providing one way information regarding the angular position of the rotational portion 110 and the linear position of the table 116. The motion control system can include position encoders and feedback to control the position of the rotational portion 110 and the table 116. The motion control system can be an open loop system, a closed loop system, or a combination of an open loop system and a closed loop system. The motion control system can use linear and rotary encoders to provide feedback related to the position of the rotational portion 110 and the position of the table 116. The motion control system can use actuators to drive the motion of the rotational portion 110 and the motion of the table 116. These positioners and actuators can include: stepper motors, DC motors, worm drives, belt drives, and other actuators known in the art.

The CT scanner also includes a data channel that routes projection measurement results from the photon counting detectors and the detector unit 103 to a data acquisition system 176, a processor 170, memory 178, network controller 174. The data acquisition system 176 controls the acquisition, digitization, and routing of projection data from the detectors. The data acquisition system 176 also includes radiography control circuitry to control the rotation of the annular rotational portion 110 and 130. In one implementation data acquisition system 176 will also control the movement of the table 116, the operation of the X-ray source 112, and the operation of the X-ray detectors. The data acquisition system 176 can be a centralized system or alternatively it can be a distributed system. In an implementation, the data acquisition system 176 is integrated with the processor 170. The processor 170 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 170 and the data acquisition system 176 can make use of the memory 178 to store, e.g., projection data, reconstructed images, calibration data and parameters, and computer programs.

The processor 170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 178 can be a hard disk drive, CD-ROM drive, DVD drive, FLASH drive, RAM, ROM or any other electronic storage known in the art.

The network controller 174, such as an Intel Ethernet PRO network interface card from Intel Corporation of America, can interface between the various parts of the CT scanner. Additionally, the network controller 174 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 2 illustrates an inner ring topology for a CT scanner. The primary difference between the CT scanner in FIG. 1 and the CT scanner in FIG. 2 is that, in FIG. 2, the X-ray source 112 and the rotational component 110 to which the X-ray source 112 is fixed are outside the circular component 120 to which the PCDs are fixed. In one implementation, the back surface of each PCD is provided a protective rear cover to shield the PCDs from irradiation from behind as the X-ray source 112 travels outside the circular component 120 of the sparsely placed photon-counting detectors.

Both the X-ray source 112, collimator 114 (e.g., a bow-tie filter), and the detector unit 103 rotate around the object OBJ in aperture 215 while the photon-counting detectors PCD1 through PCDN are stationary with respect to the object OBJ in aperture 215. In one implementation, the X-ray source 112 and collimator 114 are mounted on the first rotational component 110 mounted in the gantry 140 so that the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 having energy-integrating detectors arranged in a third-generation geometry is mounted on the second rotational component 130 that is rotatably fixed to the gantry 140. The detector unit 103 is maintained at a position diametrically opposed position from the X-ray source 112 with the object OBJ in the intermediary space between the X-ray source 112 and the detector unit 103—the rotational components 110 and 130 rotating outside the stationary circular component 120, on which the photon-counting detectors PCD1 through PCDN are fixed in a predetermined sparse arrangement.

Before a clinical CT scan, a scanogram is performed to locate anatomical landmarks and anatomical regions for scan prescription. During a scanogram scan, both the X-ray tube and the detector remain stationary, while the patient bed travels at a constant speed Image. The scanogram scan is similar to a radiograph, but no diagnostic analysis is performed in the scanogram scan. An air calibration is required before the scanogram scan. The scan image is obtained after subtracting the air scan data in log scale.

As shown in FIG. 1, in the coupled-ring photon-counting CT scanner, photon-counting detectors (PCDs) are sparsely distributed in front of the third-generation detector and behind the X-ray source. FIG. 2 illustrates, in the inner-ring photon-counting CT scanner, that PCDs are sparsely distributed in front of both the third-generation detector and the X-ray source. Thus, during scanogram scans, these PCDs create shadows on the third-generation detector and cause data missing.

Figure 3A:
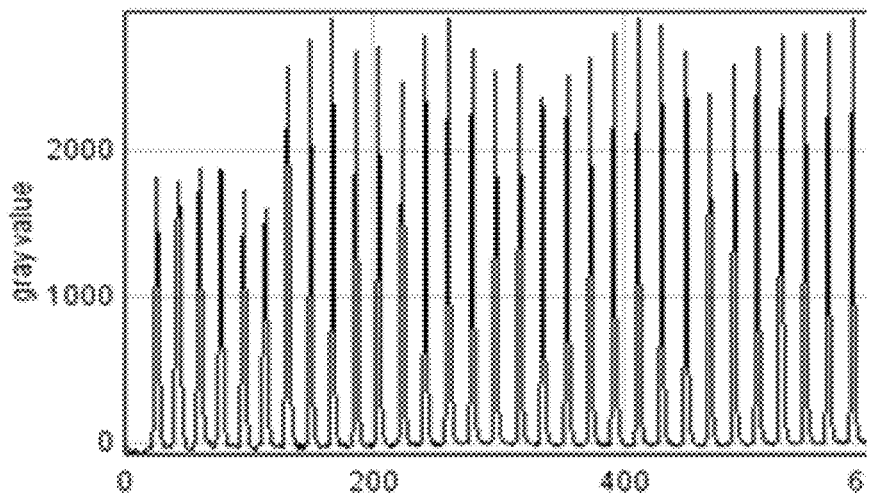
FIG. 3A illustrates exemplary shadows on a third-generation detector caused by photon-counting detectors near the third-generation detector.
Figure 3B:
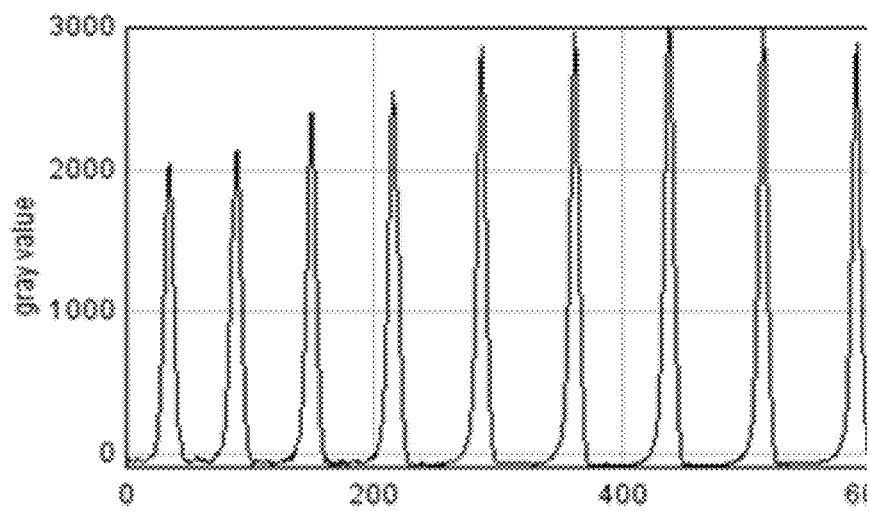
FIG. 3B illustrates exemplary shadows on the third-generation detector caused by photon-counting detectors near the X-ray tube.

FIG. 3A shows the shadows on the third-generation detector for PCDs that are near the third-generation detector. FIG. 3B shows the shadows on the third-generation detector for PCDs that are near the X-ray tube. Particularly, for the inner-ring photon-counting CT system, the PCDs at the tube side cause large shadows. These shadows can severely degrade the scanogram images.

FIG. 3C shows an exemplary scanogram of a water phantom. The left part of FIG. 3C illustrates the presence of shadows and the right part of FIG. 4C illustrates no shadows.

FIG. 3D further illustrates an exemplary scanogram profile of the water phantom with various shadows. FIG. 3E is an expanded view of FIG. 3D. When PCDs are near the X-ray tube side, the shadows occur less and are much wider. When the PCDs are near the third-generation detector, the shadows occur more frequently and are much sharper.

Furthermore, with the shadows on the third-generation detector, a traditional air calibration for scanogram is not sufficient. Typically, air calibration involves performing a scan using a CT scanner, without an object between the X-ray source and the detector. Thus, the detector array is irradiated by un-attenuated X-ray beam. The acquired air calibration data is indicative of the relative efficiency and gain of the detector array and the variation of X-ray beam intensity across the irradiation field. The air calibration data is used to normalize the attenuation data acquired during a subject scan. For CT scanners with the PCDs in front of the third-generation detector, the shadows from the PCDs need to be mapped for image processing and correction. Otherwise, the shadows can cause missing data for the third-generation detectors. Moreover, because of the variation of the actual X-ray tube position for the same target position, the shadow positions also vary slightly every time. Therefore, when scanogram scans are performed at various tube positions (e.g., 0 degrees, 90 degrees, 180 degrees, and 270 degrees), the shadow patterns are different.

Figure 4:
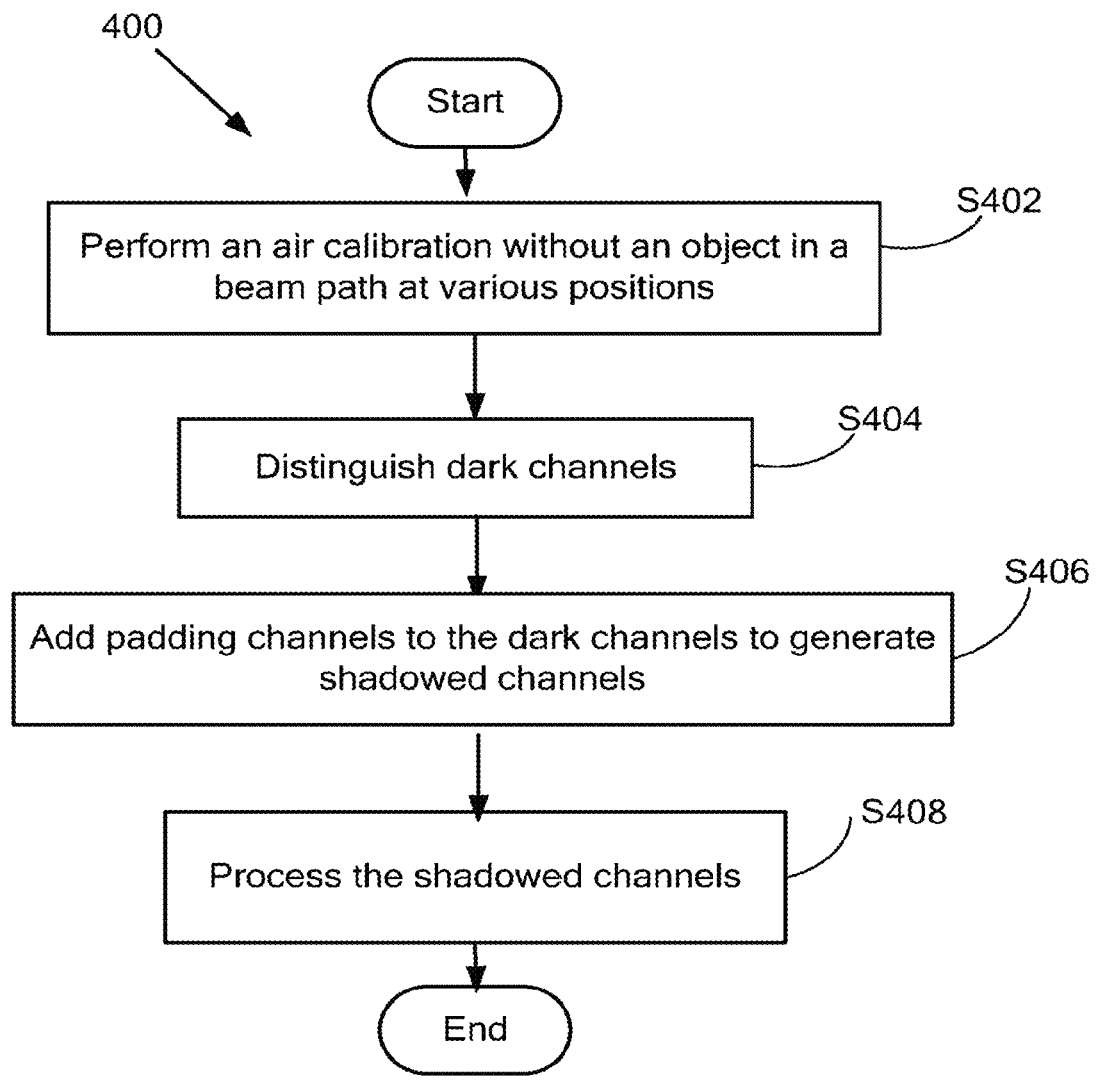
FIG. 4 illustrates a first exemplary embodiment of a shadow reduction process by way of a flowchart.

Referring to FIG. 4, a flowchart 400 describing one embodiment performed by processing circuitry for reducing the shadows effects from the sparsely distributed PCDs is shown.

In step S402, the processing circuitry performs air calibration scans at various tube positions (e.g., 0 degrees, 90 degrees, 180 degrees, and 270 degrees) without an object in the beam path. The air calibration scans can be performed at other sets of tube positions.

In step S404, the processing circuitry distinguishes dark channels, which are caused by PCD shadows, from the other channels. A threshold value is chosen, and the channels with offset-corrected raw readings that are smaller than the threshold value are selected as dark channels. The offset-corrected raw readings are obtained by subtracting dark counts as an offset from the scan data obtained in step S402. The dark counts are the response of PCDs in the absence of incident X-rays. The threshold value is determined by examining the scan data. During the air calibration performed at step S402, the shadowing blocks almost all of the irradiated X-rays. The number of detected photons in a blocked channel is close to zero (below a predetermined count) regardless of the intensity of the irradiated X-ray 504, and the number of the detected photons in an unblocked channel is much larger than the number of the detected photons in the blocked channel. Therefore, the threshold can be set based on a visual examination, which safely identifies the shadowed channels from the un-shadowed channels.

Figure 5A:
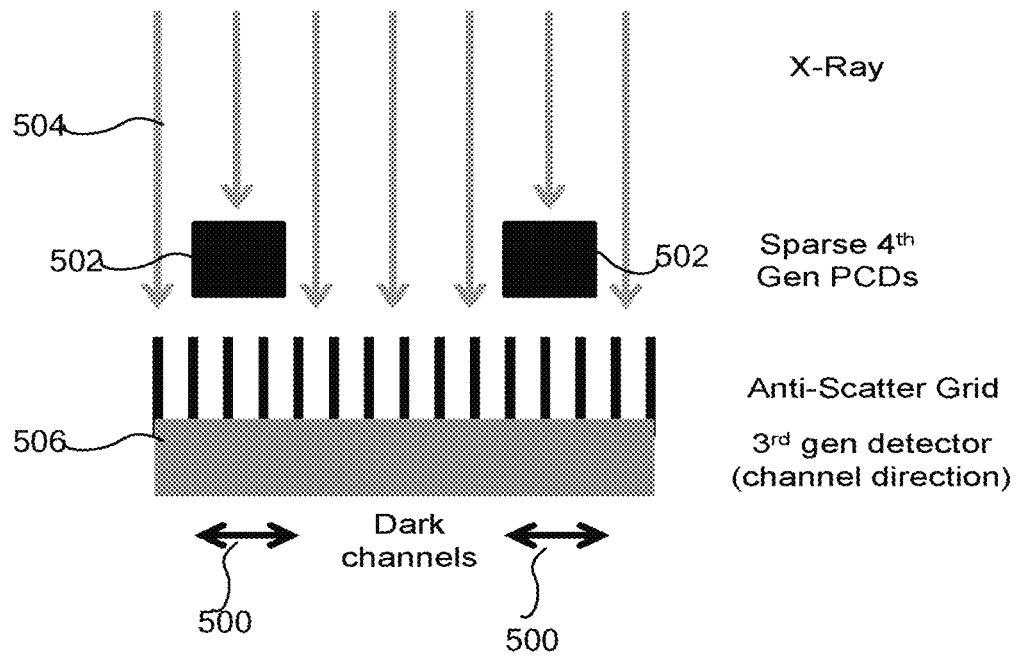
FIG. 5A illustrates exemplary dark channels on the third-generation detector.

FIG. 5A illustrates the dark channels 500 generated by the shadows of the PCDs 502. The irradiated X-ray 504 is blocked by the sparsely distributed fourth-generation PCDs 502 and the blockage of the X-ray generates the dark channels 500 on the third-generation detector 506.

Figure 5B:
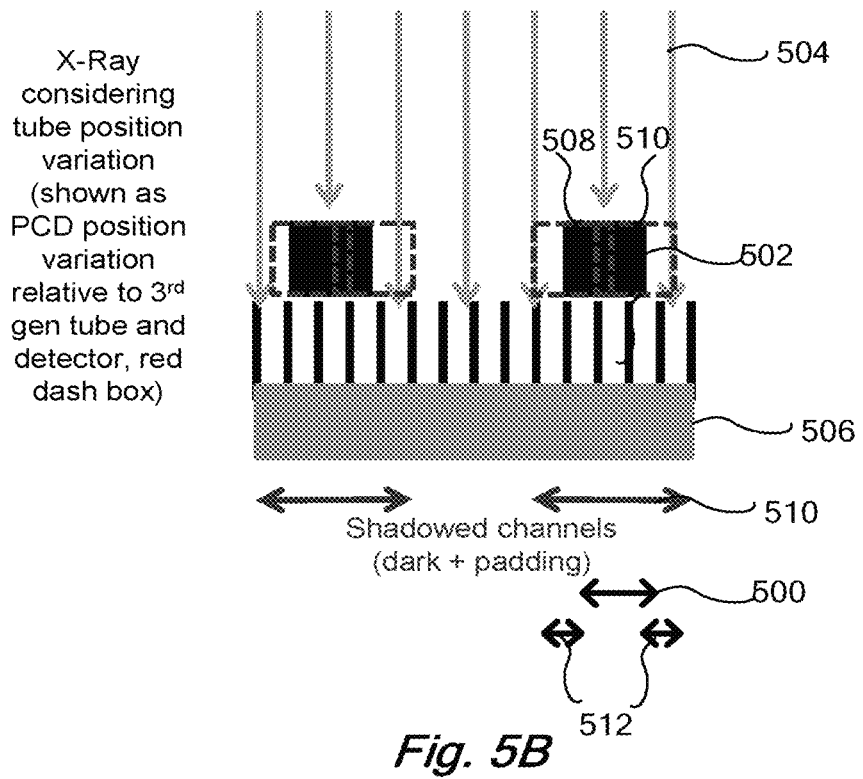
FIG. 5B illustrates exemplary shadowed channels on the third-generation detector.

In step S406, the processing circuitry adds a certain number of adjacent channels as padding channels to the dark channels to reflect the variation of the positions of the X-ray tubes. The padding channels, together with the dark channels are treated as shadowed channels. The variation of the positions of the X-ray tubes is represented as the variation of the positions of the PCDs 502. Further, the variation of the positions of the PCDs generate extra blockage of the X-ray as the padding channels. FIG. 5B illustrates that the effective positioned variation of the PCD 502 from a position 508 to a position 510 due to the tube position variation, and generate the shadowed channels 510 that includes the padding channels 512 and the dark channels 500.

In step S408, the processing circuitry processes the shadowed channels by recording numbers (locations) of the shadowed channels for each view and generating a correction map from the recorded channels.

Figure 6:
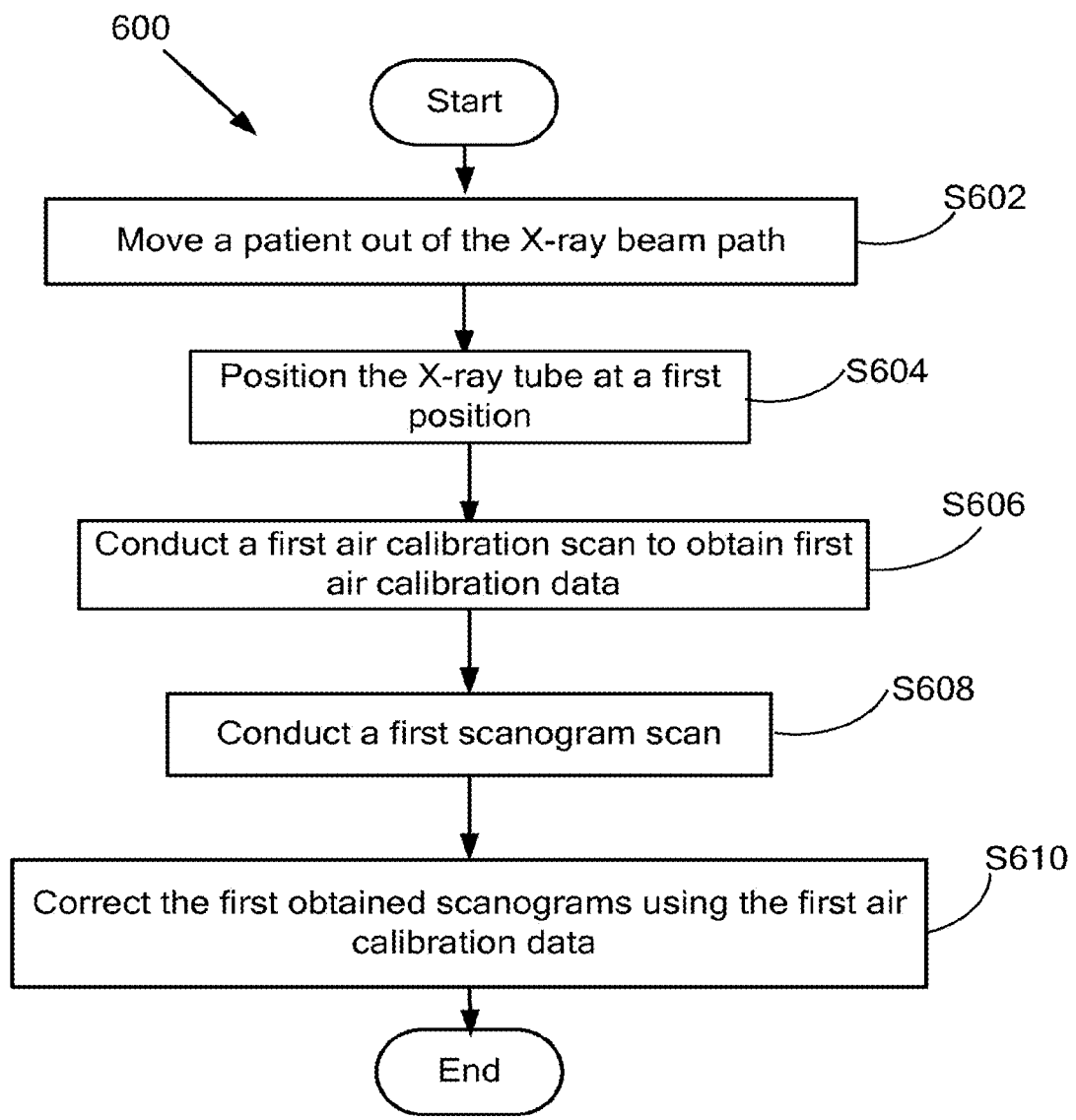
FIG. 6 illustrates a second exemplary embodiment of a shadow reduction process by way of a flowchart.

Referring to FIG. 6, a flowchart 600 describes another embodiment performed by processing circuitry to reduce the shadows effects in a single scanogram scan.

In step S602, a patient table is moved out of the X-ray beam path before performing the scanogram scan.

In step S604, the processing circuitry causes the X-ray tube to be positioned at a first position (e.g., 0 degrees, 90 degrees, 180 degrees, 270 degrees).

In step S606, the processing circuitry conducts a first air calibration scan to obtain first air calibration data.

In step S608, the processing circuitry conducts a first scanogram scan of the patient without moving the X-ray tube.

In step S610, the processing circuitry corrects the obtained scanograms using the first air calibration data. In particular, image restoration is performed on pixels impacted by shadows. The processing circuitry uses impainting techniques or interpolation to remove inconsistent data points, such as dark spots, streaks or other artifact.

For example, the scanogram is first corrected using the first air calibration data (so that both sets of data have shadows in them). This correction is simply a standard log-subtraction. Then, image restoration is performed to improve the shadowed channel data, for example, using nearest neighbor interpolation or inpainting. The goal is to remove inconsistent data points (shadows) such as dark spots, streaks, or other artifacts from the projection data. Commercial software/algorithms are available to perform this step.

In this regard, scanograms generally do not require high image quality as they are used to roughly estimate dimensions and/or compositions of the patient to help the prescription of CT protocols.

Another embodiment to reduce the shadows effects in scanogram scans is implemented by using PCD data to estimate and compensate for the shadows on the third-generation detector. The estimation uses geometrical information about the detection mechanism (e.g., distances between the detectors and sizes of the detection area). The mapping from the fourth-generation PCDs to the third-generation detector can be determined by a separate calibration procedure. A detailed mapping procedure is described below.

According to equation (1) below, the detected signal at the detector is proportional to the area of the detector, and is inversely proportional to the square of the distance between the detector and the X-ray source:

$$I_2 = I_1 \frac{A_2}{A_1}\left(\frac{R_1}{R_2}\right)^2 \quad (1)$$

wherein $I_1$ is a signal intensity of a first detector, $I_2$ is a signal intensity of a second detector, $A_1$ is an area of the first detector, $A_2$ is an area of the second detector, $R_1$ is a distance between the X-ray source and the first detector, and $R_2$ is a distance between the X-ray source and the second detector.

Since the detector unit 103 and the PCDs are different types of detectors, the detector unit 103 and the PCDs obtain different signal intensities, even under the identical irradiation conditions. Therefore, a separation calibration is performed to map the calibrated signal intensity of the PCD $I_1^c$ to the signal intensity of the detector unit 103 $I_2^c$ using:

$$I_2^c = C \times I_1^c \frac{A_D}{A_P}\left(\frac{R_P}{R_D}\right)^2 = \overline{C} \times I_1^c \quad (2)$$

wherein $$\overline{C} = \frac{I_2^c}{I_1^c} = C \times \frac{A_D}{A_P}\left(\frac{R_P}{R_D}\right)^2,$$

$I_1^c$ is a calibrated signal intensity of the PCD, $I_2^c$ is a calibrated signal intensity of the detector unit 103, $A_P$ is an area of the PCD, $A_D$ is an area of the detector unit 103, $R_P$ is a distance between the X-ray source and the PCD, $R_D$ is a distance between the X-ray source and the detector unit 103, C is a constant between the signal intensity of the PCD and the signal intensity of the detector unit, and $\overline{C}$ is a calibration constant between the calibrated signal intensity of the PCD and the signal intensity of the detector unit 103.

Theoretically, $\overline{C}$ depends on the incident spectrum. Since the object to be scanned is unknown in the calibration stage, $\overline{C}$ is extracted from the data obtained by scanning a water calibration phantom at different kVp.

Compared with previous embodiments, this approach uses the X-ray data blocked by the PCDs, and therefore is dose efficient.

Figure 7:
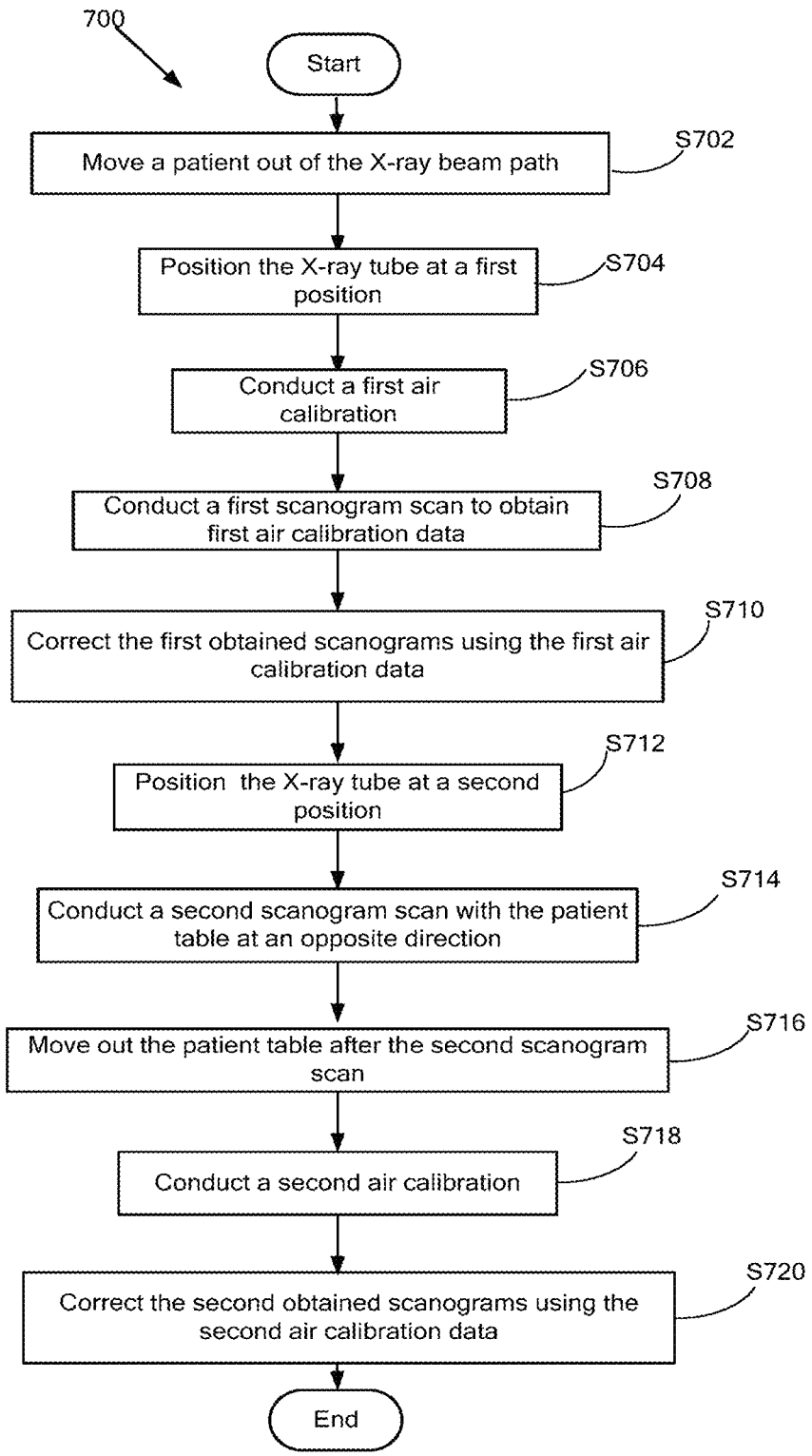
FIG. 7 illustrates a third exemplary embodiment of shadow reduction process by way of a flowchart.

Referring now to FIG. 7, a flowchart 700 describes another embodiment performed by processing circuitry to reduce the shadows effects.

Steps S702-710 are similar to steps S602-610 in the previous embodiment.

In step S712, the processing circuitry causes the X-ray tube to be positioned at a second location by rotating the gantry.

In step S714, the processing circuitry conducts a second scanogram scan of the patient while scanning the patient with the patient bed moving (in an opposite direction from the first scan) so that a range of the patient body (e.g., from neck to abdomen) is scanned. Thus, in the first scanogram, as in FIGS. 6 and 7, the patient bed is traveling into the gantry. In the second scanogram of step 714, the patient bed is traveling out of the gantry.

In step S716, the patient table is moved out of the beam path after the second scanogram scan.

In step S718, the processing circuitry conducts a second air calibration without moving the X-ray tube.

In step S720, the processing circuitry corrects the obtained second scanograms using the second air calibration data.

Note that an arbitrary number of positions can be used for the scanogram scan in this embodiment.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A computed tomography (CT) imaging apparatus, comprising:
    a radiation source configured to emit X-rays;
    a plurality of photon-counting detectors (PCDs) arranged in a circular ring between the radiation source and a CT detector; and
    processing circuitry configured to
        perform a first scan to obtain first projection data;
        determine a plurality of dark channels by comparing the obtained projection data to a predetermined threshold;
        add at least one adjacent padding channel to the determined plurality of dark channels to determine a plurality of shadowed channels;
        generate a correction map from the determined plurality of shadowed channels; and correct a scanogram obtained by a second scan based on the generated correction map.

2. The CT imaging apparatus of claim 1, wherein the processing circuitry is further configured to determine the plurality of dark channels by detecting channels having an offset-corrected raw reading that is smaller than the predetermined threshold, wherein the offset-corrected raw reading is data in which a dark count is subtracted from the first projection data, the dark count representing a response of a PCD in an absence of incident X-rays.

3. The CT imaging apparatus of claim 2, wherein the processing circuitry is further configured to determine the shadowed channels as channels with a number of detected photons that is non-zero, but less that a predetermined count.

4. The CT imaging apparatus of claim 1, wherein the processing circuitry is further configured to add a predetermined number of adjacent padding channels, which are based on tube position variations of the radiation source, to each of the determined plurality of dark channels.

5. The CT image apparatus of claim 1, wherein the processing circuitry is further configured to perform a plurality of air calibration scans at a corresponding plurality of predetermined tube positions of the radiation source.

6. The CT imaging apparatus of claim 1, wherein the processing circuitry is further configured to correct the scanogram by performing interpolation using data value adjacent to data corresponding to the shadowed channels in the correction map.

7. The CT imaging apparatus of claim 1, wherein the processing circuitry is further configured to correct the scanogram by estimating data values for the shadowed channels in the correction map using data collected by the PCDs corresponding to the shadowed channels.

8. A computed tomography (CT) imaging method that reduces shadow effects in a hybrid scanner that includes a ring of sparse, fixed photon-counting detectors (PCDs), and an X-ray source and CT detector that rotate together, the method comprising:
performing a first scan to obtain first projection data;
determining a plurality of dark channels by comparing the obtained projection data to a predetermined threshold;
adding at least one adjacent padding channel to the determined plurality of dark channels to determine a plurality of shadowed channels;
generating a correction map from the determined plurality of shadowed channels; and
correcting a scanogram obtained by a second scan based on the generated correction map.

9. The CT imaging method of claim 8, wherein the adding step comprises adding a predetermined number of adjacent padding channels, which are based on tube position variations of the X-ray source, to each of the determined plurality of dark channels.

10. The CT image method of claim 8, wherein the performing step comprises performing a plurality of air calibration scans at a corresponding plurality of predetermined tube positions of the X-ray source.

11. The CT imaging method of claim 8, wherein the correcting step comprises performing interpolation using data value adjacent to data corresponding to the shadowed channels in the correction map.

12. The CT imaging method of claim 8, wherein the correcting step comprises estimating data values for the shadowed channels in the correction map using data collected by the PCDs corresponding to the shadowed channels.

* * * * *